US00PP28623P3

(12) United States Plant Patent
NeSmith

(10) Patent No.: US PP28,623 P3
(45) Date of Patent: Nov. 14, 2017

(54) RABBITEYE BLUEBERRY PLANT NAMED 'T-1101'

(50) Latin Name: *Vaccinium ashei*
Varietal Denomination: T-1101

(71) Applicant: University of Georgia Research Foundation, Inc., Athens, GA (US)

(72) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 106 days.

(21) Appl. No.: 14/756,565

(22) Filed: Sep. 17, 2015

(65) Prior Publication Data

US 2017/0086343 P1 Mar. 23, 2017

(51) Int. Cl.
*A01H 5/08* (2006.01)

(52) U.S. Cl.
USPC ..... Plt./157

(58) Field of Classification Search
USPC ..... Plt./156, 157
See application file for complete search history.

(56) References Cited

PUBLICATIONS

NeSmith, Scott. 2011. Blueberry Cultivar Development at the University of Georgia: A progress report for 2011. http://www.smallfruits.org/blueberries/production/alap11rep.pdf. Accessed Mar. 28, 2017. 13 pages.*

* cited by examiner

*Primary Examiner* — Susan McCormick Ewoldt
*Assistant Examiner* — Karen Redden
(74) *Attorney, Agent, or Firm* — Klarquist Sparkman, LLP

(57) ABSTRACT

The new variety 'T-1101' ripens around late May in southern Georgia and mid June in middle Georgia. The fruit of the new variety 'T-1101' are very large, firm, have good flavor and scar. The new variety 'T-1101' is vigorous with an estimated chilling requirement of about 400 to 450 hours at or below approximately 7° C. The asexually reproduced variety is reliably propagated vegetatively.

4 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'T-1101' is a rabbiteye blueberry plant that is a *Vaccinium ashei.*

Variety denomination: The new rabbiteye blueberry plant claimed is of the variety denominated 'T-1101'.

BACKGROUND OF THE INVENTION

The present invention relates to the discovery of a new and distinct cultivar of rabbiteye blueberry plant botanically known as a *Vaccinium ashei* and herein referred to as 'T-1101', as herein described and illustrated.

The new blueberry plant variety 'T-1101' was selected in Griffin, Ga. in 2007. The new variety 'T-1101' ripens around late May in southern Georgia. The fruit of the new variety 'T-1101' are large, with favorable firmness and good flavor. The new variety 'T-1101' has good yield and is vigorous with an estimated chilling requirement of about 400-450 hours at or below 7° C.

Pedigree and history: 'T-1101' was selected in 2007 in Griffin, Ga., originating from seed of open pollinated 'Vernon' fruit collected by Dr. Scott NeSmith in 2004. The maternal parent, 'Vernon', is a 2004 release and the subject of U.S. Plant Pat. No. 18,291. The paternal parent is unknown. 'T-1101' was first asexually propagated by softwood cutting in Griffin, Ga. commencing in 2007. The new 'T-1101' selection has been tested in plantings in Alapaha and Griffin, Ga. since 2009. This new variety has also recently been asexually propagated by tissue culture.

SUMMARY OF THE INVENTION

The new blueberry plant variety 'T-1101' has not been observed under all possible environmental conditions. The phenotype may vary somewhat with variations in environment and cultural practices such as temperature and light intensity without, however, any variance in genotype.

The following traits have been repeatedly observed in the original plant and in asexually propagated plants of the new variety, propagated by softwood cuttings, growing in Alapaha and Griffin Ga., and are determined to be the unique firmly fixed combination of characteristics of the new blueberry plant variety 'T-1101':

1. Large berry size;
2. Favorable scar;
3. Good berry flavor;
4. Favorable berry firmness.

The new variety 'T-1101' can be compared to the rabbiteye blueberry varieties 'T-959' which is the subject of U.S. Plant Pat. No. 24,135), 'Vernon' (the subject of U.S. Plant Pat. No. 18,291), and 'Alapaha' (the subject of U.S. Plant Pat. No. 16,266).

Comparison: The selection ripens with 'Vernon' and 'Alapaha' in the early Georgia rabbiteye season. 'T-1101' has large, firm berries with good flavor as compared to 'T-959', 'Vernon' and 'Alapaha' standards growing in Alapaha and Griffin, Ga. over a 4-year period (Tables 1 and 2). Table 3 describes berry weight, firmness and Brix for 'T-1101' as compared to the 'Alapaha', 'Vernon', and 'T-959' rabbiteye blueberry cultivars for the years 2012-2013. 'T-1101' had larger berry weight than 'Alapaha' and 'Vernon' and comparable berry weight to 'T-959'. 'T-1101' had the highest Brix compared with 'Vernon' and 'T-959'. Table 4 describes the berry weight and yield for 'T-1101' compared to 'Vernon' for the years 2013 to 2014. Over the two year period of observation, 'T-1101' had greater average yield per bush than 'Vernon'. 'T-1101' is slightly to moderately susceptible to fruit splitting.

The major attraction of 'T-1101' is its large berry size, allowing for more efficient hand harvesting than exhibited by other rabbiteye varieties. 'T-959' and 'T-1101' can be used for pollinating each other.

TABLE 1

4-year average ratings of some fruit and plant characteristics of 'T-1101' and standard cultivars 'Alapaha', 'Vernon', and 'T-959' from 2011-2014 in field test plots at Alapaha, GA. Rating scales are based on a 1 to 10 score, with 1 being the least desirable and 10 being the most desirable. A value of 6-7 is generally considered to be the minimum acceptable rating for a commercial cultivar. These plants were established in 2009.

| Berry and plant | Alapaha location | | | |
|---|---|---|---|---|
| attributes[1/] | 'T-1101' | 'Alapaha' | 'Vernon' | 'T-959' |
| Berry size | 9.3 ± 0.1 | 6.3 ± 0.1 | 7.9 ± 0.1 | 8.9 ± 0.2 |
| Berry scar | 7.4 ± 0.2 | 7.4 ± 0.1 | 7.2 ± 0.1 | 7.5 ± 0.2 |
| Berry color | 7.2 ± 0.2 | 6.7 ± 0.1 | 7.1 ± 0.1 | 7.0 ± 0.1 |
| Berry firmness | 7.8 ± 0.1 | 6.9 ± 0.1 | 7.5 ± 0.2 | 8.3 ± 0.2 |
| Berry flavor | 7.2 ± 0.1 | 7.1 ± 0.1 | 7.3 ± 0.1 | 6.8 ± 0.1 |
| Cropping | 6.1 ± 0.5 | 6.8 ± 1.0 | 4.5 ± 0.9 | 5.2 ± 0.8 |
| Plant vigor | 8.6 ± 0.1 | 8.0 ± 0.3 | 9.2 ± 0.3 | 9.5 ± 0.3 |
| Date of 50% flowering | March 16 | March 26 | March 21 | March 24 |
| Date of 50% ripening | May 28 | June 4 | June 1 | June 2 |
| Fruit development period (days) | 78 ± 3.7 | 73 ± 2.0 | 75 ± 3.0 | 75 ± 1.6 |

[1/]Values are means ± the standard error with n = 4.

TABLE 2

4-year average ratings of some fruit and plant characteristics of 'T-1101' and standard cultivars 'Alapaha', 'Vernon', and 'T-959' (2011-2014) in field test plots at Griffin, GA. Rating scales are based on a 1 to 10 score, with 1 being the least desirable and 10 being the most desirable. A value of 6-7 is generally considered to be the minimum acceptable rating for a commercial cultivar. These plants were established in 2009.

| Berry and plant | Griffin location | | | |
|---|---|---|---|---|
| attributes[1/] | 'T-1101' | 'Alapaha' | 'Vernon' | 'T-959' |
| Berry size | 8.7 ± 0.2 | 6.5 ± 0.2 | 7.7 ± 0.1 | 8.8 ± 0.3 |
| Berry scar | 7.4 ± 0.1 | 7.3 ± 0.1 | 7.1 ± 0.1 | 7.6 ± 0.4 |
| Berry color | 7.3 ± 0.3 | 7.0 ± 0.1 | 7.2 ± 0.1 | 7.1 ± 0.1 |
| Berry firmness | 7.4 ± 0.1 | 6.9 ± 0.1 | 7.5 ± 0.2 | 8.5 ± 0.3 |
| Berry flavor | 7.1 ± 0.2 | 7.3 ± 0.2 | 7.5 ± 0.2 | 7.0 ± 0.1 |
| Cropping | 6.6 ± 0.7 | 7.5 ± 0.9 | 6.2 ± 0.5 | 7.1 ± 1.0 |
| Plant vigor | 7.4 ± 0.4 | 7.5 ± 0.3 | 8.8 ± 0.1 | 9.5 ± 0.2 |
| Date of 50% flowering | March 24 | April 1 | April 2 | April 3 |
| Date of 50% ripening | June 16 | June 13 | June 13 | June 18 |

TABLE 2-continued 4-year average ratings of some fruit and plant characteristics of 'T-1101' and standard cultivars 'Alapaha', 'Vernon', and 'T-959' (2011-2014) in field test plots at Griffin, GA. Rating scales are based on a 1 to 10 score, with 1 being the least desirable and 10 being the most desirable. A value of 6-7 is generally considered to be the minimum acceptable rating for a commercial cultivar. These plants were established in 2009.

| Berry and plant | Griffin location | | | |
|---|---|---|---|---|
| attributes[1/] | 'T-1101' | 'Alapaha' | 'Vernon' | 'T-959' |
| Fruit development period (days) | 84 ± 1.9 | 76 ± 1.6 | 76 ± 2.1 | 80 ± 3.9 |

[1/]Values are means ± the standard error with n = 4.

TABLE 3

Berry weight, firmness, and Brix for 'Alapaha', 'Vernon', and 'T-959' cultivars and 'T-1101' grown in Griffin, GA during 2012-2013.

| Year | 'T-1101' | 'Alapaha' | 'Vernon' | 'T-959' |
|---|---|---|---|---|
| | Berry wt (g/berry) [1/] | | | |
| 2012 | 2.92 ± 0.07 | 1.28 ± 0.06 | 1.60 ± 0.05 | 2.60 ± 0.06 |
| 2013 | 3.08 ± 0.10 | 1.63 ± 0.04 | 2.43 ± 0.09 | 3.10 ± 0.08 |
| Avg | 3.0 | 1.46 | 2.01 | 2.85 |
| | Firmness (g/mm) [1/] | | | |
| 2012 | 198 ± 5 | 175 ± 4 | 185 ± 4 | 240 ± 7 |
| 2013 | 168 ± 3 | 169 ± 4 | 164 ± 6 | 220 ± 5 |
| Avg | 183 | 172 | 175 | 230 |
| | Brix (%) [2/] | | | |
| 2012 | 12.7 ± 0.3 | 10.8 ± 0.4 | 11.5 ± 0.5 | 10.2 ± 0.3 |
| 2013 | 13.0 ± 0.5 | 13.2 ± 0.3 | 10.0 ± 0.5 | 10.0 ± 0.1 |
| Avg | 12.9 | 12.0 | 10.8 | 10.1 |

[1/] Values are means ± the standard error with n = 3 (each sample derived from 25 berry avg).
[2/] Values are means ± the standard error with n = 3 (each sample derived from 5 berry composite).

TABLE 4

Yield and berry weight 'Vernon' and 'T-1101' grown in Alapaha, GA during 2012-2013.

| Year | 'T-1101' | 'Vernon' |
|---|---|---|
| | Berry wt (g/berry) [1/] | |
| 2013 | 2.75 ± 0.09 | 1.93 ± 0.08 |
| 2014 | 2.90 ± 0.08 | 2.14 ± 0.09 |
| Avg | 2.83 | 2.03 |
| | Yield (lbs/plant) [2/] | |
| 2013 | 12.5 ± 0.4 | 9.5 ± 1.9 |
| 2014 | 24.0 ± 1.5 | 21.6 ± 1.3 |
| Avg | 18.3 | 15.6 |

[1/] Values are means ± the standard error with n = 3 (each sample derived from 25 berry avg).
[2/] Values are means ± the standard error with n = 3.

BRIEF DESCRIPTION OF THE FIGURES

The accompanying photographic illustrations show typical specimens in full color of the foliage, flowering, and fruit of the new variety 'T-1101'. The colors are as nearly true as is reasonably possible in a color representation of this type.

BOTANICAL DESCRIPTION

Figure 1:
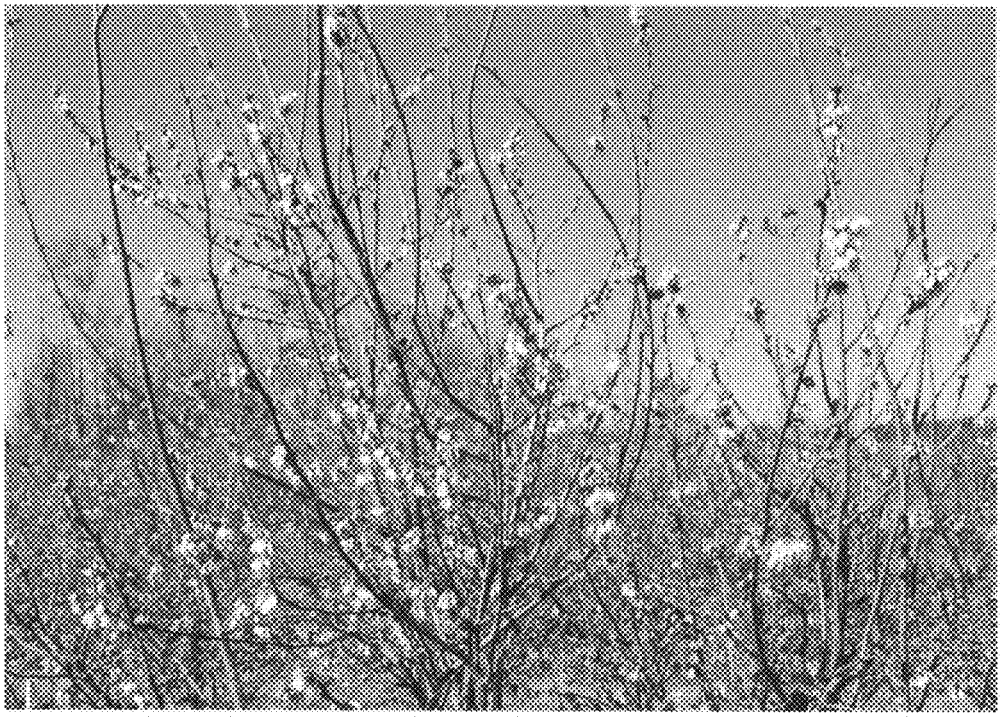
FIG. 1 is a photograph of a five year old plant of the new variety 'T-1101' during flowering in Alapaha, Ga.
Figure 2:
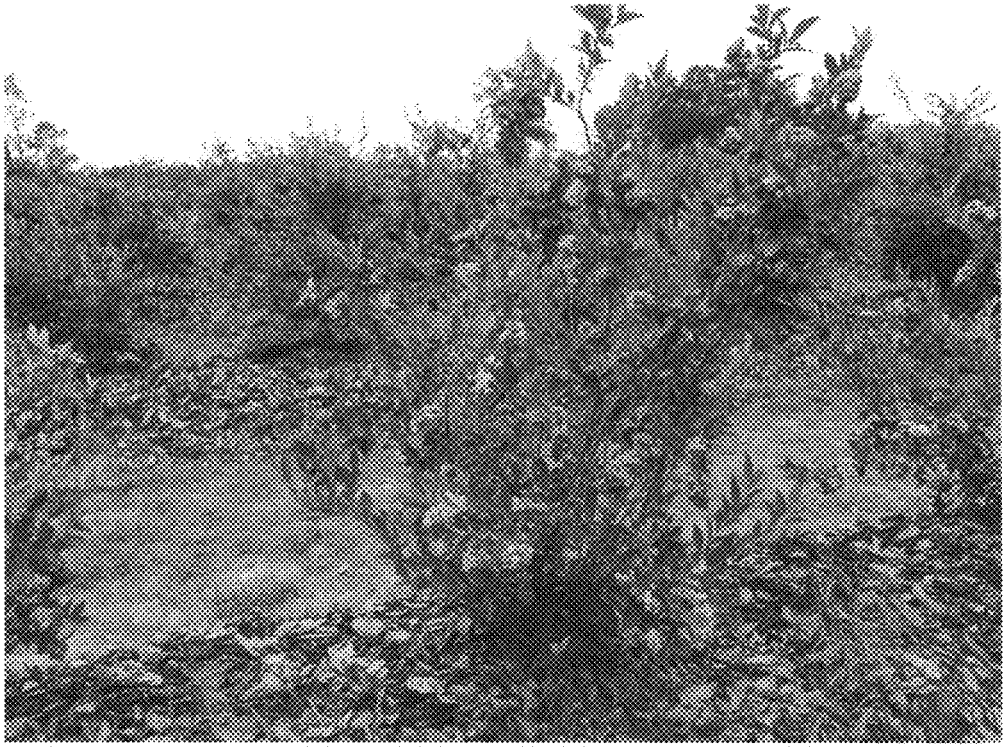
FIG. 2 is a photograph of a three year old plant of the new variety 'T-1101' during fruit ripening in Alapaha, Ga.
Figure 3:
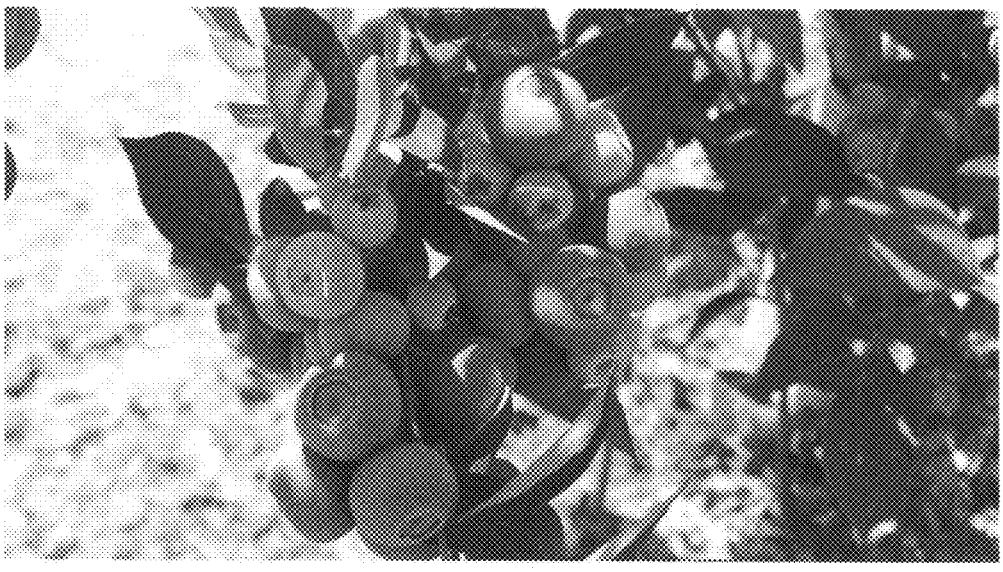
FIG. 3 is a close up photograph of a fruit cluster of a three year old plant of the new variety 'T-1101'.
Figure 4:
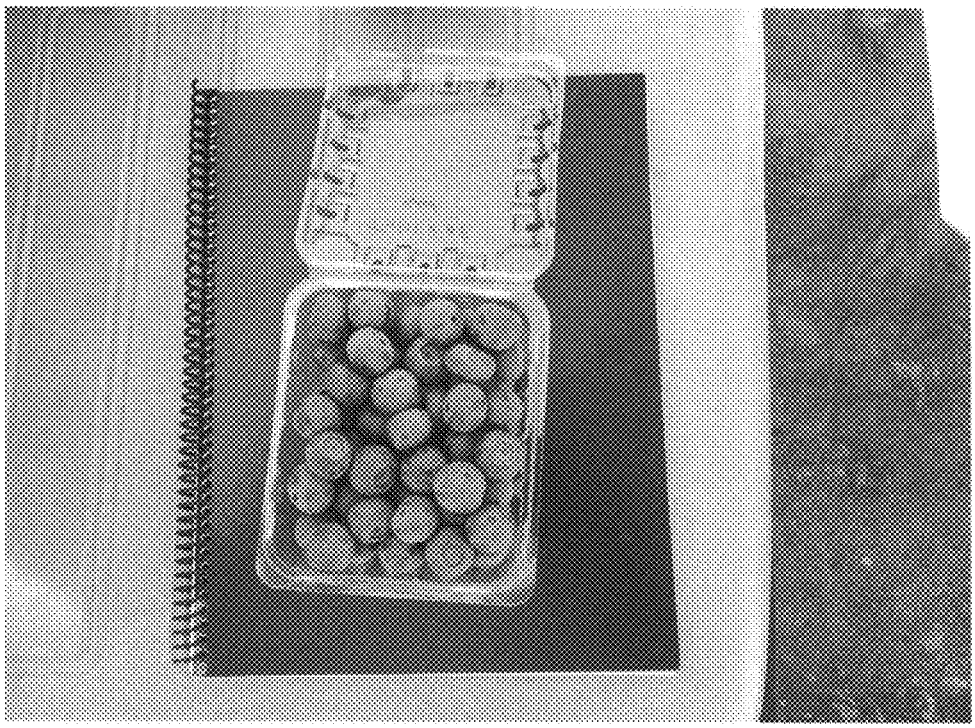
FIG. 4 is a photograph of harvested fruit of the new variety 'T-1101'

Throughout this specification, color names beginning with a small letter signify that the name of that color, as used in common speech, is aptly descriptive. Color names beginning with a capital letter designate values based upon The Royal Horticultural Society Colour Chart, 5$^{th}$ edition (hereinafter R.H.S.) published by The Royal Horticultural Society, London, England.

The following is a detailed description of the botanical and pomological characteristics of the new variety 'T-1101'. Where dimensions, sizes, colors, and other characteristics are given, it is to be understood that such characteristics are approximations and averages set forth as accurately as practicable. The descriptions reported herein are largely from observations of specimen plants grown in Alapaha and Griffin, Ga., with supplemental irrigation. The observed plants were about 4 to about 5 years old.

PLANT

Size: 1.6 to 2.2 m tall by about 4 years of age. The plant crown, or base, is narrow, typically 15 to 30 cm in diameter. Upper portion of plant canopy exceeds 1.2 to 1.5 m in diameter by 4 years.

Growth habit: Strongly upright, with 3 to 5 main canes arising from a narrow crown, and multiple branching of shoots from those canes at 15 cm or more above the soil surface.

Growth: Highly vigorous.

Productivity: High crop and yield, averaging 15 to 20 lbs of fruit per plant each year for plants 4 years and older grown under well fertilized and irrigated field conditions.

Hardiness: Similar to other rabbiteye cultivars such as 'Vernon' and 'T-959'.

Chilling requirement: 400-450 hours of temperatures at or below 7° C. (about 45° F.) to induce normal leafing and flowering during the spring under conventional production systems. The chill requirement is less than the maternal parent 'Vernon' (500-550 hours of chilling required).

Leafing: Plants tend to break sufficient leaf buds simultaneously with, or shortly after, anthesis.

Canes:

- *Diameter.*—20 to 35 mm for base of main canes that are about 4 years old and older. 10 to 15 mm in about 2 year old wood. 5 to 10 mm in current season wood.
- *Color.*—Greyed-Green RHS 197C for base of canes that are about 4 years old and older. Yellow-Green RHS 144B transitioning to Greyed-Brown RHS 199B in about 2 year old wood. Yellow-Green RHS 144B in current season wood.

Disease resistance: No exceptional disease resistance or susceptibility observed; typical for rabbiteye 'Vernon' and 'T-959'. The variety shows a tendency for some fruit cracking during maturity following certain rain conditions.

FOLIAGE

Leaf color: Healthy mature leaves.
- *Top side.*—Green RHS 137B to Green RHS 137C.
- *Under side.*—Green RHS 138B to Green RHS 138C.

Leaf arrangement: Alternate, simple.

Leaf shape: Lanceolate to oblanceolate.

Leaf surface: Both upper and lower leaf surfaces are glaucous.

Leaf margins: Crenate to serrulate, smooth.

Leaf venation: Pinnate with slight netting.

Leaf apices: Narrowly acute to acuminate.

Leaf bases: Cuneate.

Leaf dimensions:
- *Length.*—50.0 to 65.0 mm.
- *Width.*—20.0 to 25.0 mm.

Petioles: Small.
- *Length.*—2.5 to 3.0 mm.
- *Width.*—1.5 to 2.0 mm.
- *Color.*—Yellow-Green RHS 144D.

FLOWERS

Date of 50% anthesis: March 16 in southern Georgia and March 24 in middle Georgia (4 year average).

Flower shape: Urceolate to tubular.

Flower bud number: High, averaging 6 to 9 buds per fruiting shoot.

Flowers per cluster: 7 to 9 common.

Flower fragrance: None.

Corolla:
- *Color.*—White RHS 155C to White RHS NN155C (open flower).
- *Length.*—8.5 to 9.5 mm.
- *Width.*—5.5 to 6.5 mm.
- *Aperture width.*—2.5 to 3.0 mm.

Flower peduncle:
- *Length.*—5.0 to 6.5 mm.
- *Color.*—Yellow-Green RHS 145D.

Flower pedicel:
- *Length.*—3.0 to 3.5 mm.
- *Color.*—Green RHS 138C.

Calyx (with sepals):
- *Diameter.*—4.0 to 4.5 mm.
- *Color.*—Green RHS 138B (lower surface is the calyx, upper surface is the ovary, both are Green RHS 138B).

Sepal:
- *Shape.*—More or less triangular.
- *Number.*—Typically 5, fused about halfway down.
- *Length.*—0.8 to 1.4 mm.
- *Width.*—1.0 to 1.5 mm.
- *Apex.*—Most are typically rounded, sometimes lightly pointed tips are observed.
- *Margins.*—Smooth.
- *Texture.*—Mostly smooth, both surfaces.

Stamen:
- *Length.*—8.5 to 9.0 mm.
- *Number per flower.*—10.
- *Filament color.*—Green-White RHS 157B to 157C.

Style:
- *Length.*—8.5 to 9.5 mm.
- *Color.*—Yellow-Green RHS 138D.

Pistil:

*Length.*—11.0 to 12.0 mm.

*Ovary color* (*exterior*).—Green RHS 138B.

Anther:

*Length.*—4.0 to 4.5 mm.

*Number.*—10.

*Color.*—Greyed-Orange RHS 165B.

Pollen:

*Abundance.*—Medium to high.

*Color.*—Yellow-White RHS 158A.

Self-compatibility: The cultivar has a small degree of self-compatibility.

FRUIT

Date of 50% maturity: May 28 in southern Georgia and June 16 in middle Georgia (4 year average).

Fruit development period: 74 to 84 days.

Berry color:

*With wax.*—Violet-Blue RHS 97C.

*With wax removed.*—Black RHS 202A.

Berry surface wax abundance: High.

Berry flesh color: White RHS NN155A.

Berry weight:

*First harvest.*—2.3 g to 3.6 g.

*Second harvest.*—2.0 g to 2.8 g.

Berry size:

*Height from calyx to scar.*—13.0 to 17.0 mm.

*Diameter.*—16.0 to 21.0 mm.

Berry shape: Semi-spherical.

Fruit stem scar: Medium, dry, no tearing at harvest.

Calyx: Depth 4.0 to 5.0 mm; width 6.0 to 8.0 mm; sepals generally not present.

Berry firmness: Very good.

Berry flavor and texture: Flavor is good, texture is good; firm skin and berry flesh.

Berry cluster: Depends upon fruit set, typically four to six.

Storage quality: Very good.

Suitability for mechanical harvesting: Likely very suitable.

Uses: Can be used as fresh fruit for shipping, but also customer-pick and processing markets.

Harvest date averages: First harvest date is May $20^{th}$ in South Georgia. Second harvest date is May $28^{th}$ in South Georgia and June $16^{th}$ in Middle Georgia.

SEED

Seed abundance in fruit: Medium to high, with 15 or more fully developed seeds per berry.

Seed color: Greyed-Orange RHS 165B.

Seed dry weight: 49.3 mg per 100 seeds.

Seed size: 1.4 to 1.8 mm long; 0.7 to 1.0 mm wide for fully developed seeds.

What is claimed is:

1. A new and distinct variety of rabbiteye blueberry plant named 'T-1101', substantially as illustrated and described herein.

* * * * *